US010806854B2

(12) United States Patent
O'Connor et al.

(10) Patent No.: US 10,806,854 B2
(45) Date of Patent: Oct. 20, 2020

(54) INSERTION MECHANISM FOR A DRUG DELIVERY PUMP

(71) Applicant: UNL Holdings LLC, New York, NY (US)

(72) Inventors: Sean M. O'Connor, West Chester, PA (US); Robert Decker, Dillsburg, PA (US); Gautam N. Shetty, Pikesville, MD (US); Mark A. DeStefano, Collegeville, PA (US); Ian B. Hanson, Wayne, PA (US); Paul F. Bente, IV, Chesterbrook, PA (US)

(73) Assignee: UNL Holdings LLC, New York, NY (US)

(*) Notice: Subject to any disclaimer, the term of this patent is extended or adjusted under 35 U.S.C. 154(b) by 868 days.

(21) Appl. No.: 15/369,125

(22) Filed: Dec. 5, 2016

(65) Prior Publication Data
US 2017/0080149 A1 Mar. 23, 2017

Related U.S. Application Data

(63) Continuation of application No. 13/599,727, filed on Aug. 30, 2012, now Pat. No. 9,511,189.
(Continued)

(51) Int. Cl.
A61M 5/158 (2006.01)
A61M 5/142 (2006.01)

(52) U.S. Cl.
CPC ........ A61M 5/158 (2013.01); A61M 5/14248 (2013.01); A61M 2005/14252 (2013.01);
(Continued)

(58) Field of Classification Search
CPC ......... A61M 2005/14252; A61M 2005/14284; A61M 2005/1583; A61M 2005/1585;
(Continued)

(56) References Cited

U.S. PATENT DOCUMENTS 3,336,924 A 8/1967 Sarnoff et al.
3,401,692 A 9/1968 Harris, Jr.
(Continued)

FOREIGN PATENT DOCUMENTS

CN 1245077 A 2/2000
CN 101557847 A 10/2009
(Continued)

OTHER PUBLICATIONS

U.S. Food and Drug Administration, "Infusion Pump Improvement Initiative," Apr. 2010, 6 pp.
(Continued)

Primary Examiner — Bhisma Mehta
Assistant Examiner — Larry R. Wilson
(74) Attorney, Agent, or Firm — Hamilton, Brook, Smith & Reynolds, P.C.

(57) ABSTRACT

An insertion mechanism for a drug pump includes an insertion mechanism housing; a manifold guide; an insertion biasing members initially held in an energized state; a retraction biasing member and a hub connected to a proximal end of a needle, wherein the retraction biasing member is held initially in an energized state between the hub and the manifold guide; and a manifold having a septum and a cannula, wherein the annular space between the septum and the cannula defines a manifold header. The needle and cannula are inserted into the body of a user by the insertion biasing member(s), after which only the needle is retracted. Retraction of the needle may open a fluid pathway from the manifold header to the body through the cannula. A drug delivery pump includes an activation mechanism, a drive mechanism, a fluid pathway connection, and the insertion mechanism. Assembly and operation methods are provided.

21 Claims, 8 Drawing Sheets

Related U.S. Application Data

(60) Provisional application No. 61/530,774, filed on Sep. 2, 2011.

(52) U.S. Cl.
CPC ............... *A61M 2005/1583* (2013.01); *A61M 2005/1585* (2013.01)

(58) Field of Classification Search
CPC .......... A61M 39/0208; A61M 39/0247; A61M 2039/0232; A61M 2039/0258; A61M 2039/0261; A61M 2039/0291; A61M 2005/14256; A61M 2005/1426; A61M 2005/1587
See application file for complete search history.

(56) References Cited

U.S. PATENT DOCUMENTS

| | | | |
|---|---|---|---|
| 3,413,974 A | 12/1968 | Cohen | |
| 3,778,971 A | 12/1973 | Granger et al. | |
| 3,940,003 A | 2/1976 | Larson | |
| 4,004,586 A | 1/1977 | Christensen et al. | |
| 4,048,997 A | 9/1977 | Raghavachari et al. | |
| 4,565,543 A | 1/1986 | Bekkering et al. | |
| 4,673,400 A | 6/1987 | Martin | |
| 4,685,903 A | 8/1987 | Cable et al. | |
| 4,755,173 A | 7/1988 | Konopka et al. | |
| 4,840,620 A | 6/1989 | Kobayashi et al. | |
| 5,147,311 A | 9/1992 | Pickhard | |
| 5,167,816 A | 12/1992 | Kruger et al. | |
| 5,795,339 A | 8/1998 | Erskine | |
| 5,851,197 A | 12/1998 | Marano et al. | |
| 5,858,001 A | 1/1999 | Tsals et al. | |
| 6,248,093 B1 | 6/2001 | Moberg | |
| 6,368,314 B1 | 4/2002 | Kipfer et al. | |
| 6,699,218 B2 | 3/2004 | Flaherty et al. | |
| 7,063,684 B2 | 6/2006 | Moberg | |
| 7,250,037 B2 | 7/2007 | Shermer et al. | |
| D564,087 S | 3/2008 | Yodfat et al. | |
| D585,543 S | 1/2009 | Yodfat et al. | |
| 7,479,135 B2 | 1/2009 | Richter et al. | |
| D586,463 S | 2/2009 | Evans et al. | |
| 7,611,503 B2 | 11/2009 | Spohn et al. | |
| 7,780,636 B2 | 8/2010 | Radmer et al. | |
| 7,803,134 B2 | 9/2010 | Sharifi et al. | |
| D629,503 S | 12/2010 | Caffey et al. | |
| 7,846,132 B2 | 12/2010 | Gravesen et al. | |
| 7,879,010 B2 | 2/2011 | Hunn et al. | |
| 7,905,859 B2 | 3/2011 | Bynum et al. | |
| 7,927,306 B2 | 4/2011 | Cross et al. | |
| 7,967,795 B1 | 6/2011 | Cabiri | |
| 8,029,472 B2 | 10/2011 | Leinsing et al. | |
| 8,048,031 B2 | 11/2011 | Shaw et al. | |
| 8,152,771 B2 | 4/2012 | Mogensen et al. | |
| 8,157,769 B2 | 4/2012 | Cabiri | |
| 8,162,892 B2 | 4/2012 | Mogensen et al. | |
| 8,167,844 B2 | 5/2012 | Dillard, III | |
| 8,187,232 B2 | 5/2012 | Chong et al. | |
| D669,165 S | 10/2012 | Estes et al. | |
| 8,409,145 B2 | 4/2013 | Raymond et al. | |
| D684,685 S | 6/2013 | Schneider et al. | |
| D684,686 S | 6/2013 | Cronenberg | |
| D685,083 S | 6/2013 | Schneider et al. | |
| 8,591,465 B2 | 11/2013 | Hommann | |
| D709,183 S | 7/2014 | Kemlein | |
| 8,795,234 B2 | 8/2014 | Kadamus et al. | |
| D723,157 S | 2/2015 | Clemente et al. | |
| 9,005,169 B2 | 4/2015 | Gravesen et al. | |
| D745,142 S | 12/2015 | O'Connor et al. | |
| D752,442 S | 3/2016 | O'Donahue | |
| 9,463,280 B2 | 10/2016 | Cabiri | |
| 9,511,189 B2 | 12/2016 | O'Connor et al. | |
| 2003/0199816 A1 | 10/2003 | Ramming | |
| 2004/0069044 A1 | 4/2004 | Lavi et al. | |
| 2004/0092878 A1 | 5/2004 | Flaherty | |
| 2007/0010789 A1 | 1/2007 | Peter et al. | |
| 2007/0179444 A1 | 8/2007 | Causey et al. | |
| 2007/0282269 A1 | 12/2007 | Carter et al. | |
| 2008/0065029 A1 | 3/2008 | Racz | |
| 2008/0132842 A1 | 6/2008 | Flaherty | |
| 2008/0269683 A1* | 10/2008 | Bikovsky ............ A61M 5/1413 604/164.12 |
| 2008/0269687 A1 | 10/2008 | Chong et al. | |
| 2009/0124979 A1 | 5/2009 | Raymond et al. | |
| 2009/0204077 A1 | 8/2009 | Hasted et al. | |
| 2009/0240240 A1 | 9/2009 | Hines et al. | |
| 2010/0049129 A1* | 2/2010 | Yokoi .................. A61M 5/158 604/136 |
| 2010/0130932 A1 | 5/2010 | Yodfat et al. | |
| 2010/0331824 A1 | 12/2010 | Moberg et al. | |
| 2011/0054390 A1 | 3/2011 | Searle et al. | |
| 2011/0098652 A1 | 4/2011 | Hasted et al. | |
| 2011/0160678 A1 | 6/2011 | Chong et al. | |
| 2011/0166509 A1 | 7/2011 | Gross et al. | |
| 2011/0270188 A1 | 11/2011 | Caffey et al. | |
| 2011/0306929 A1 | 12/2011 | Levesque et al. | |
| 2012/0035546 A1 | 2/2012 | Cabiri | |
| 2012/0096953 A1 | 4/2012 | Bente, IV et al. | |
| 2012/0123354 A1 | 5/2012 | Woehr | |
| 2012/0211946 A1 | 8/2012 | Halili et al. | |
| 2013/0060196 A1 | 3/2013 | O'Connor et al. | |
| 2013/0060233 A1 | 3/2013 | O'Connor et al. | |
| 2013/0066274 A1 | 3/2013 | O'Connor et al. | |
| 2013/0131595 A1 | 5/2013 | Ekman et al. | |
| 2017/0224915 A1 | 8/2017 | DeStefano et al. | |

FOREIGN PATENT DOCUMENTS

| | | |
|---|---|---|
| CN | 101631585 A | 1/2010 |
| CN | 101947337 A | 1/2011 |
| EP | 589328 A2 | 3/1994 |
| EP | 1219283 A2 | 7/2002 |
| EP | 1702635 A2 | 9/2006 |
| EP | 1341569 B1 | 1/2007 |
| EP | 1427471 B1 | 2/2008 |
| EP | 1695727 B1 | 7/2008 |
| EP | 1513580 B1 | 3/2009 |
| EP | 2077128 A1 | 7/2009 |
| EP | 2269559 A2 | 1/2011 |
| EP | 2331190 A1 | 6/2011 |
| EP | 2379134 A1 | 10/2011 |
| EP | 2429612 A1 | 3/2012 |
| EP | 2433663 A1 | 3/2012 |
| EP | 2731642 B1 | 9/2018 |
| JP | 2002-524217 A | 8/2002 |
| JP | 2003-527159 A | 9/2003 |
| JP | 2004-195227 A | 7/2004 |
| JP | 2004-528939 A | 9/2004 |
| JP | 2010-501211 A | 1/2010 |
| JP | 2010-501281 A | 1/2010 |
| JP | 2010-528810 A | 8/2010 |
| JP | 2010526633 A | 8/2010 |
| JP | 2010-531196 A | 9/2010 |
| JP | 2010-538751 A | 12/2010 |
| JP | 2011-045537 A | 3/2011 |
| JP | 2011-511689 A | 4/2011 |
| WO | WO 95/19194 A1 | 7/1995 |
| WO | WO 99/48546 A1 | 9/1999 |
| WO | WO 00/15292 A2 | 3/2000 |
| WO | 2000/029049 A1 | 5/2000 |
| WO | WO 01/30424 A1 | 5/2001 |
| WO | WO 03/024504 A2 | 3/2003 |
| WO | WO 03/103763 A1 | 12/2003 |
| WO | WO 2004/035116 A1 | 4/2004 |
| WO | WO 2004/062714 A1 | 7/2004 |
| WO | WO 2005/037350 A2 | 4/2005 |
| WO | WO 2005/044344 A1 | 5/2005 |
| WO | WO 2006/129196 A1 | 12/2006 |
| WO | 2008/024810 A2 | 2/2008 |
| WO | WO 2008/024808 A2 | 2/2008 |
| WO | WO 2008/105954 A2 | 9/2008 |
| WO | WO 2008/133702 A1 | 11/2008 |
| WO | WO 2008/153460 A1 | 12/2008 |

(56) References Cited

FOREIGN PATENT DOCUMENTS

| WO | 2009/039013 A1 | 3/2009 |
|---|---|---|
| WO | WO 2009/101145 A1 | 8/2009 |
| WO | WO 2010/029054 A1 | 3/2010 |
| WO | WO 2010/077807 A1 | 7/2010 |
| WO | WO 2010/084113 A1 | 7/2010 |
| WO | WO 2010/085338 A1 | 7/2010 |
| WO | WO 2010/112377 A1 | 10/2010 |
| WO | WO 2010/132196 A1 | 11/2010 |
| WO | WO 2010/139672 A1 | 12/2010 |
| WO | WO 2011/006652 A1 | 1/2011 |
| WO | WO 2011/046950 A1 | 4/2011 |
| WO | WO 2011/090956 A2 | 7/2011 |
| WO | WO 2011/121023 A1 | 10/2011 |
| WO | WO 2012/032411 A2 | 3/2012 |
| WO | WO 2012/131044 A1 | 10/2012 |
| WO | 2013/033421 A2 | 3/2013 |
| WO | WO 2013/033467 A2 | 3/2013 |
| WO | WO 2013/156224 A1 | 10/2013 |
| WO | 2014/011879 A2 | 1/2014 |
| WO | 2016/053954 A1 | 4/2016 |

OTHER PUBLICATIONS

Meng et al., "MEMS-enabled implantable drug infusion pumps for laboratory animal research, preclinical, and clinical applications," *Adv. Drug. Deily. Rev.*, 64(14), Nov. 2012, pp. 1628-1638.

European Patent Office, International Search Report in International Application No. PCT/US2012/053174, dated Mar. 28, 2013, 4 pp.

European Patent Office, International Search Report in International Application No. PCT/US2012/053241, dated Feb. 28, 2013, 6 pp.

European Patent Office, International Search Report in International Patent Application No. PCT/US2012/054861, dated Feb. 18, 2013.

European Patent Office, Written Opinion of the International Searching Authority in International Application No. PCT/US2012/053174, dated Mar. 28, 2013, 6 pp.

European Patent Office, Written Opinion of the International Searching Authority in International Application No. PCT/US2012/053241, dated Feb. 28, 2013, 8 pp.

Preliminary Amendment and Application Data Sheet Filed in National Phase of WO 2011/090956 A2 (U.S. Appl. No. 13/521,181) (dated Jul. 9, 2012).

Final Office Action for U.S. Appl. No. 13/599,727, entitled "Insertion Mechanism for a Drug Delivery Pump" dated Dec. 1, 2014.

International Preliminary Report on Patentability for Int'l Application No. PCT/US2012/053174, titled: Insertion Mechanism for a Drug Delivery Pump, dated Mar. 17, 2014.

International Preliminary Report on Patentability for Int'l Application No. PCT/US2012/053174, titled: Insertion Mechanism for a Drug Delivery Pump, dated Sep. 25, 2014.

Non-Final Office Action for U.S. Appl. No. 13/599,727, entitled "Insertion Mechanism for a Drug Delivery Pump" dated Aug. 14, 2014.

Non-Final Office Action for U.S. Appl. No. 13/599,727, entitled "Insertion Mechanism for a Drug Delivery Pump" dated Feb. 16, 2016.

Notice of Allowance for U.S. Appl. No. 13/599,727, entitled "Insertion Mechanism for a Drug Delivery Pump" dated Jun. 29, 2016.

Notice of Allowance for U.S. Appl. No. 13/599,727, entitled "Insertion Mechanism for a Drug Delivery Pump" dated Oct. 14, 2016.

* cited by examiner

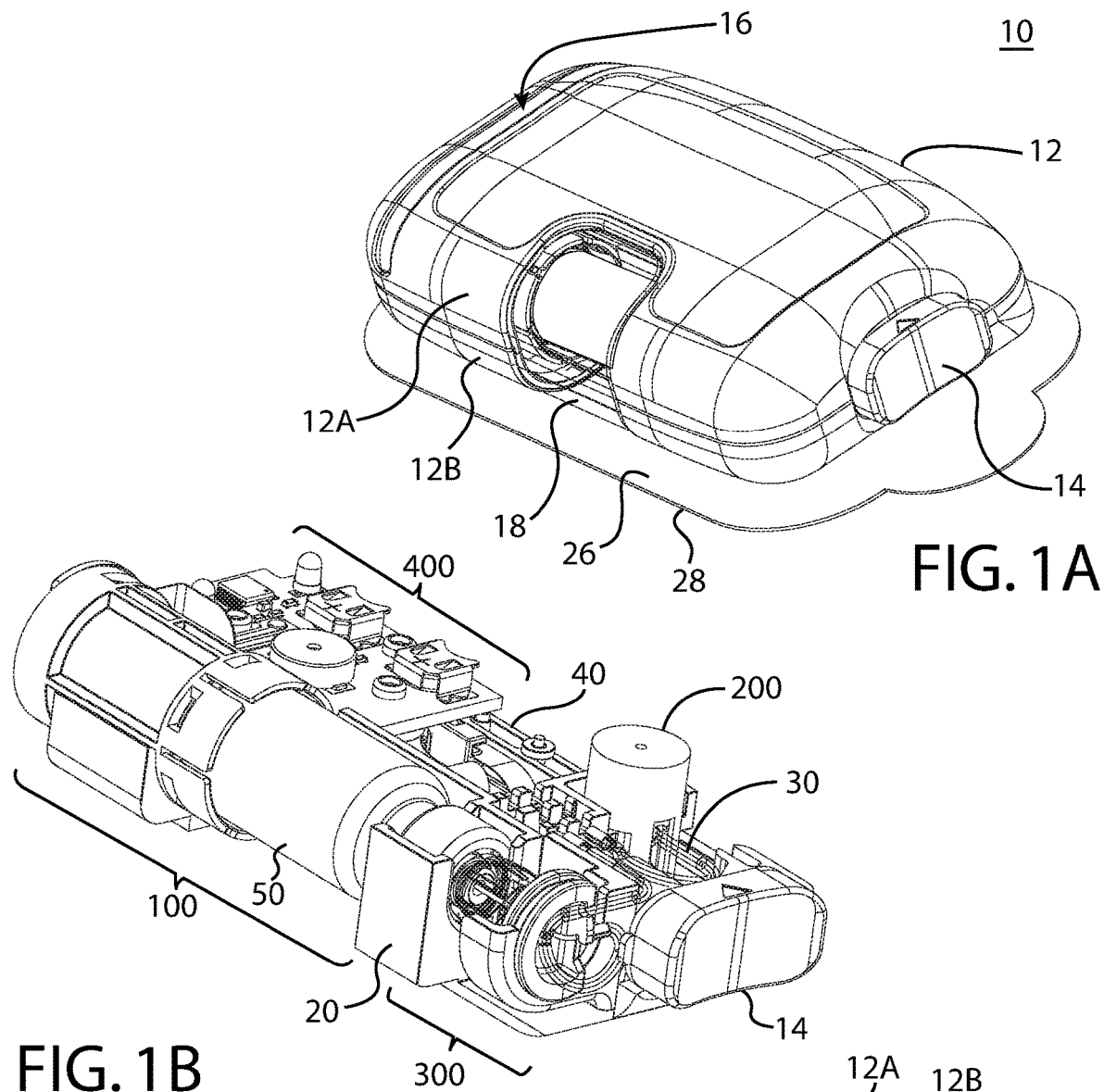
FIG. 1A
FIG. 1B
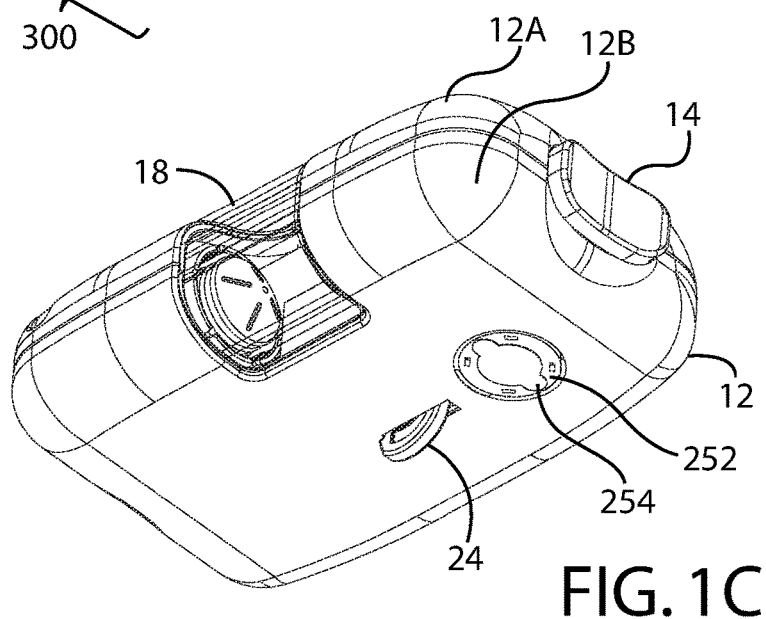
FIG. 1C

INSERTION MECHANISM FOR A DRUG DELIVERY PUMP

CROSS-REFERENCE TO RELATED APPLICATIONS

This application is a continuation of U.S. application Ser. No. 13/599,727, filed Aug. 30, 2012, which claims priority to U.S. Provisional Application No. 61/530,774, filed on Sep. 2, 2011, each of which is included by reference herein in its entirety for all purposes.

FIELD

THIS INVENTION relates to drug delivery pumps. More particularly, this invention relates to insertion mechanisms for drug delivery pumps, drug delivery pumps with safety integrated insertion mechanisms, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The present invention provides insertion mechanisms for drug delivery pumps, drug delivery pumps with safety integrated insertion mechanisms, the methods of operating such devices, and the methods of assembling such devices. The insertion mechanisms of the present invention provide integrated safety features which automatically retract the needle into the device while retaining the cannula within the body of the user to, for example, minimize pain and discomfort associated with drug delivery. Additionally, the embodiments of the present invention provide sterile fluid pathways through the novel insertion mechanisms and drug pumps, which pathways are only engaged, connected, or opened upon proper activation by the user. Accordingly, the novel devices of the present invention alleviate one or more of the problems associated with prior art devices, such as those referred to above.

In a first embodiment, the present invention provides an insertion mechanism for a drug pump, said insertion mechanism including: an insertion mechanism housing having an internal chamber; a manifold guide having an upper chamber and a lower chamber separated by a manifold guide ring; one or more insertion biasing members initially held in an energized state within the internal chamber of insertion mechanism housing between the housing and the manifold guide ring; a clip flexibly engaged with the upper chamber of the manifold guide; a retraction biasing member and a hub connected to a proximal end of a needle, wherein the retraction biasing member is held initially in an energized state between the hub and the manifold guide; and a manifold having a septum and a cannula, wherein the annular space between the septum and the cannula defines a manifold header. In an alternative embodiment, the insertion mechanism may include two or more insertion biasing members. The manifold has a manifold intake for connection to a fluid conduit.

The insertion mechanism may further include a base connected to a distal end of the insertion mechanism housing. A sterile boot may be fixedly connected between the manifold and the base connected to a distal end of the insertion mechanism housing. The term "sterile boot" is used to describe a boot within which certain internal components may reside, at one or more stages of operation, in a sterile condition. The boot need not be sterile through the entire operation of the mechanism or pump and, in fact, may not be initially sterile until assembly and sterilization of certain components has occurred. Additionally, the term "boot" is not intended to mean any specific shape or configuration, but is instead utilized to describe a component that can provide an interior space within which other components may reside at one or more stages of operation. One or more guide protrusions may extend from a proximal end of the insertion mechanism housing into the internal chamber. Alternatively, the one or more guide protrusions may be a separate component that is fixed to the insertion mechanism housing. The manifold guide ring has one or more pass-throughs which correspond with the guide protrusions, wherein the manifold guide is slidably engaged with the housing by interaction between the pass-throughs and the guide protrusions. The interaction between the pass-throughs and the guide protrusions may also function to maintain the rotational alignment of the manifold guide and/or to promote proper assembly of the components. The insertion mechanism may further include a ferrule which maintains the cannula in a fixed and sealed position within the manifold.

The clip may have one or more arms, with each arm having a release surface and a lockout surface. In an initial locked configuration the release surfaces engage the hub to maintain the retraction biasing member in an energized state; and, in a retracted configuration the release surfaces disengage the hub to permit de-energizing of the retraction biasing member, thereby retracting the hub and the needle. In the retracted configuration, the cannula is maintained in the inserted position within the body of the user by the fixed and/or sealed manifold connection enabled by the ferrule. The cannula, manifold, and manifold guide are maintained in their final positions and prevented from axial translation in the proximal direction by interaction between the lockout surfaces of the clips and the distal ends of the guide protrusions, effectively locking out further motion of these components.

In another embodiment, the present invention provides a drug delivery pump with integrated safety features includes a housing and an assembly platform, upon which an activation mechanism, a drive mechanism, a fluid pathway connection, a power control system, and an insertion mechanism for a drug pump may be mounted, said insertion mechanism including: an insertion mechanism housing having an internal chamber; a manifold guide having an upper chamber and a lower chamber separated by a manifold guide ring; one or more insertion biasing members initially held in an energized state within the internal chamber of insertion mechanism housing between the housing and the manifold guide ring; a clip flexibly engaged with the upper chamber of the manifold guide; a retraction biasing member and a hub connected to a proximal end of a needle, wherein the retraction biasing member is held initially in an energized state between the hub and the manifold guide; a manifold having a septum and a cannula, wherein the annular space between the septum and the cannula defines a manifold header; and a base for connection of the insertion mechanism to the assembly platform.

The insertion mechanism of the drug pump may further include a base connected to a distal end of the insertion mechanism housing. The manifold may have a manifold intake for connection to a fluid conduit, wherein the fluid conduit is employable for fluid transfer between the fluid pathway connection and the insertion mechanism. A sterile boot may be fixedly connected between the manifold and the base connected to a distal end of the insertion mechanism housing. These components function to maintain the sterility of the fluid pathway, the needle, and the cannula prior to insertion into the body of the user. Retraction of the needle from the cannula, as described further herein, may be utilized to open a fluid pathway from the manifold header through the cannula to the body of the user.

In a further embodiment, the present invention provides a method of assembling the insertion mechanism includes the steps of: connecting a hub to a proximal end of a needle; inserting the hub and needle into an inner upper chamber of a manifold guide, wherein a retraction biasing member is maintained in an energized state between the manifold guide and the hub, and maintained in the energized state by a clip fixedly and flexibly connected to the manifold guide at a clip interface. The method further includes: inserting a cannula into a manifold and inserting a septum into the manifold at an end opposing the cannula to create a manifold header there-between, and subsequently inserting the manifold, septum, and cannula into a lower chamber of the manifold guide such that the needle pierces through the septum and resides initially at least partially within the cannula. Furthermore, the method includes: inserting an insertion biasing member into an insertion mechanism housing between the housing and one or more guide protrusions extending into the interior of the housing from a proximal end; inserting the manifold guide into the insertion mechanism housing such that the guide protrusions extend through corresponding pass-throughs on a manifold guide ring aspect of the manifold guide, wherein as the manifold guide is translated in the proximal direction, the insertion biasing member is caused to contact the manifold guide ring and become energized.

Upon translation of the manifold guide and compression of the insertion biasing member to a point above one or more lockout windows of the insertion mechanism housing, the method includes the step of: placing one or more corresponding lockout pin(s) into the lockout windows and in removable engagement with the manifold guide to retain the manifold guide in this position and the insertion biasing member in the energized state. Finally, a base may be attached to the distal end of the insertion mechanism housing to maintain the components in position. The method of assembly may further include the step of: attaching a sterile boot in fixed engagement at a proximal end to the manifold and in a fixed engagement at a distal end to the base. Similarly, the method may include: attaching a fluid conduit to the manifold at a manifold intake.

In yet another embodiment, the present invention provides a method of operating the drug delivery pump. The method of operation includes: displacing an activation mechanism to disengage one or more lockout pins from corresponding lockout windows of an insertion mechanism housing, wherein such disengagement permits an insertion biasing member to expand in a distal direction substantially along a longitudinal axis of the insertion mechanism housing from its initial energized state, wherein such expansion drives insertion of a needle and a cannula into the body of a user. The method further includes: disengaging one or more release surfaces of a clip from engagement with a hub retained within a manifold guide within the insertion mechanism housing, wherein such disengagement permits a retraction biasing member to expand in a proximal direction substantially along a longitudinal axis of the insertion mechanism housing from its initial energized state, wherein such expansion drives retraction of the needle while retaining the cannula into the body of a user; connecting a fluid pathway connection having a piercing member to a drug container having a pierceable seal; and activating a drive mechanism to force a fluid through the fluid pathway connection, the cannula, and into the body of a user. In a preferred embodiment, the method of operation may include: first displacing one or more on-body sensors to permit displacement of the activation mechanism. Retraction of the needle from the cannula opens a fluid pathway from the fluid pathway connection to the cannula, for delivery of a drug fluid to the body of a user.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 1A shows an isometric view of a drug delivery pump having safety integrated insertion mechanisms, according to one embodiment of the present invention;

FIG. 1B shows an isometric view of the interior components of the drug delivery pump shown in FIG. 1A;

FIG. 1C shows an isometric view of the bottom of the drug delivery pump shown in FIG. 1A;

DETAILED DESCRIPTION

Figure 2A:
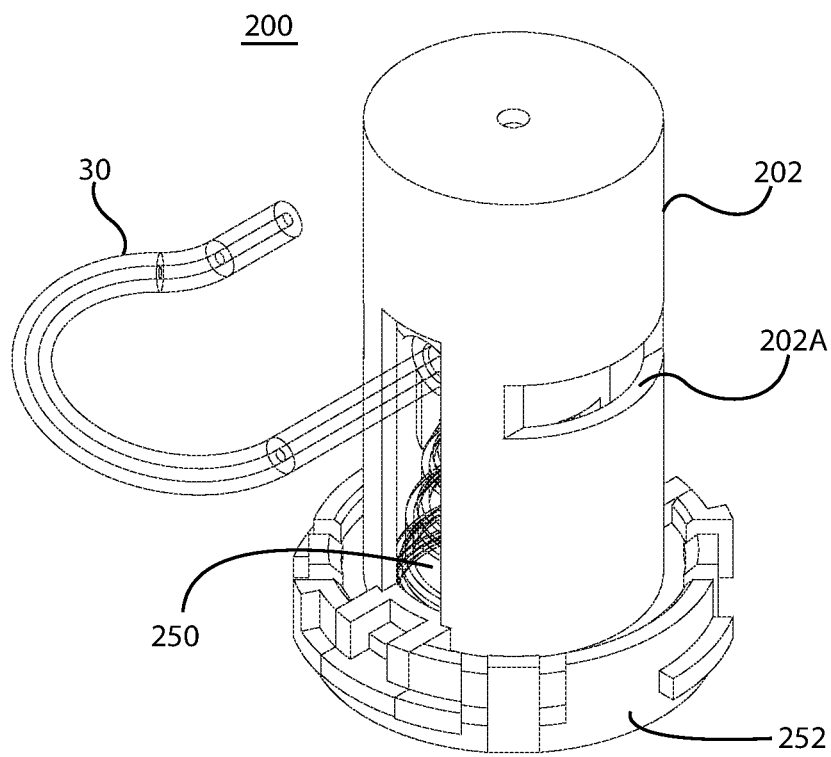
FIG. 2A shows an isometric view of an insertion mechanism, according to a first embodiment of the present invention.

As used herein to describe the insertion mechanisms, drug delivery pumps, or any of the relative positions of the components of the present invention, the terms "axial" or "axially" refer generally to a longitudinal axis "A" around which the insertion mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of syringes. According to various aspects and embodiments described herein, reference is made to a "biasing member", such as in the context of one or more biasing members for insertion or retraction of the needle, trocar, and/or cannula. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

The novel devices of the present invention provide insertion mechanisms with integrated safety features and drug delivery pumps which incorporate such insertion mechanisms. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pump, insertion mechanism, and their respective components are described further herein with reference to the accompanying figures.

Drug Delivery Pump:

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump further includes assembly platform 20, sterile fluid conduit 30, drive mechanism 100 having drug container 50, insertion mechanism 200, fluid pathway connection 300, and power and control system 400. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the body of the user. Housing 12 is described in further detail hereinafter with reference to other components and embodiments of the present invention.

Drug pump is configured such that, upon activation by a user by depression of the activation mechanism, the drug pump is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIG. 1C) may be provided in one embodiment as a safety feature to ensure that the power and control system 400, or the activation mechanism, cannot be engaged unless the drug pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system 400 will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14. During the drug delivery process, the power and control system 400 is configured to provide a dispensing status signal via the status indicator 16. After the drug has been administered into the body of the user and after the end of any additional dwell time, to ensure that substantially the entire dose has been delivered to the user, the power and control system 400 may provide an okay-to-remove status signal via the status indicator 16. This may be independently verified by the user by viewing the drive mechanism and drug dose delivery through the window 18 of the pump housing 12. Additionally, the power and control system 400 may be configured to provide one or more alert signals via the status indicator 16, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Fluid Pathway Connection:

The fluid pathway connection 300 includes a sterile fluid conduit 30, a piercing member, a connection hub, and a sterile sleeve. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In a preferred embodiment, this connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

The drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Drive Mechanism:

The drive mechanism 100 includes drug container 50 having a cap, a pierceable seal, and a plunger seal. The drug container may contain a drug fluid, within the container between the cap and the plunger seal, for delivery through the insertion mechanism and drug pump into the body of the user. The drive mechanism may further include one or more drive biasing members, one or more release mechanisms, and one or more guides. The components of the drive mechanism function to force a fluid from the drug container out through the pierceable seal or, preferably, through the piercing member of the fluid pathway connection for delivery through the fluid pathway connection, sterile fluid conduit, and insertion mechanism into the body of the user.

The drive mechanism may further include one or more electrical contacts located on corresponding components which, upon contact between electrical contacts, are capable of continuing an energy pathway or otherwise relay a signal to and/or from the power and control system 400. Such signals may be transferred across one or more interconnects. Such components may be utilized within the drive mechanism to measure and relay information related to the status of operation of the drive mechanism, which may be converted by the power and control system 400 into tactile, auditory, and/or visual feedback to the user.

In one particular embodiment, the drive mechanism 100 employs one or more compression springs as the biasing member(s). Upon activation of the drug pump by the user, the power and control system may be actuated to directly or indirectly release the compression spring(s) from an energized state. Upon release, the compression spring(s) may bear against and act upon the plunger seal to force the fluid drug out of the drug container. The fluid pathway connection is connected through the pierceable seal prior to, concurrently with, or after activation of the drive mechanism to permit fluid flow from the drug container, through the fluid pathway connection, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

Figure 3A:
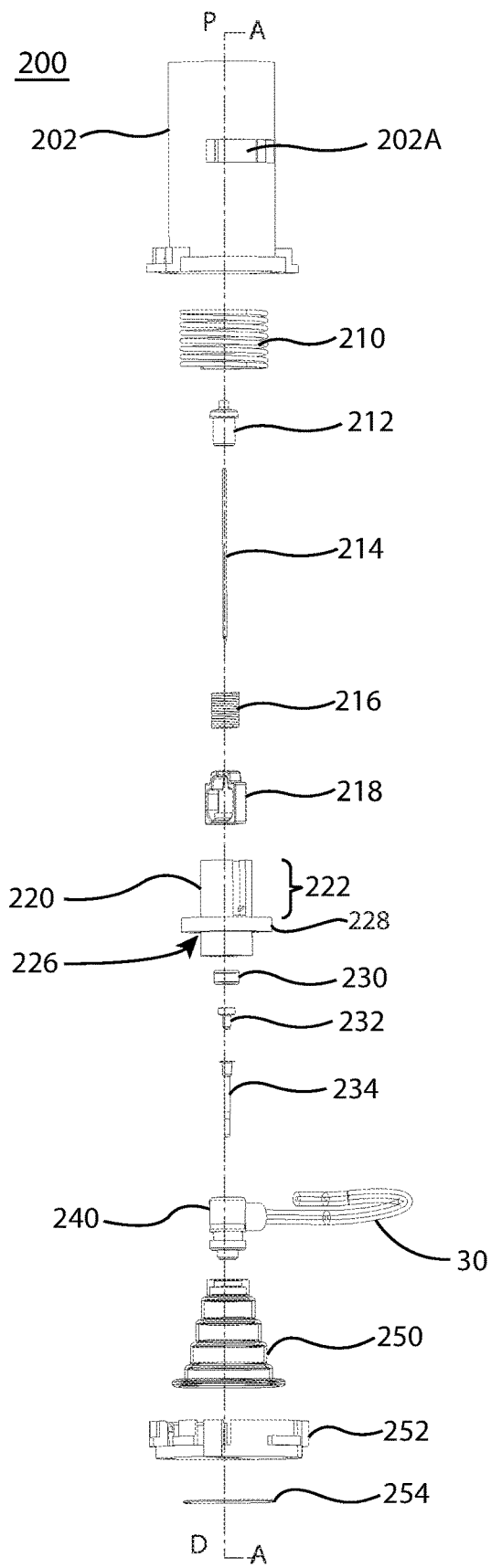
FIG. 3A shows an exploded view, exploded along an axis "A," of the insertion mechanism shown in FIG. 2A.
Figure 3B:
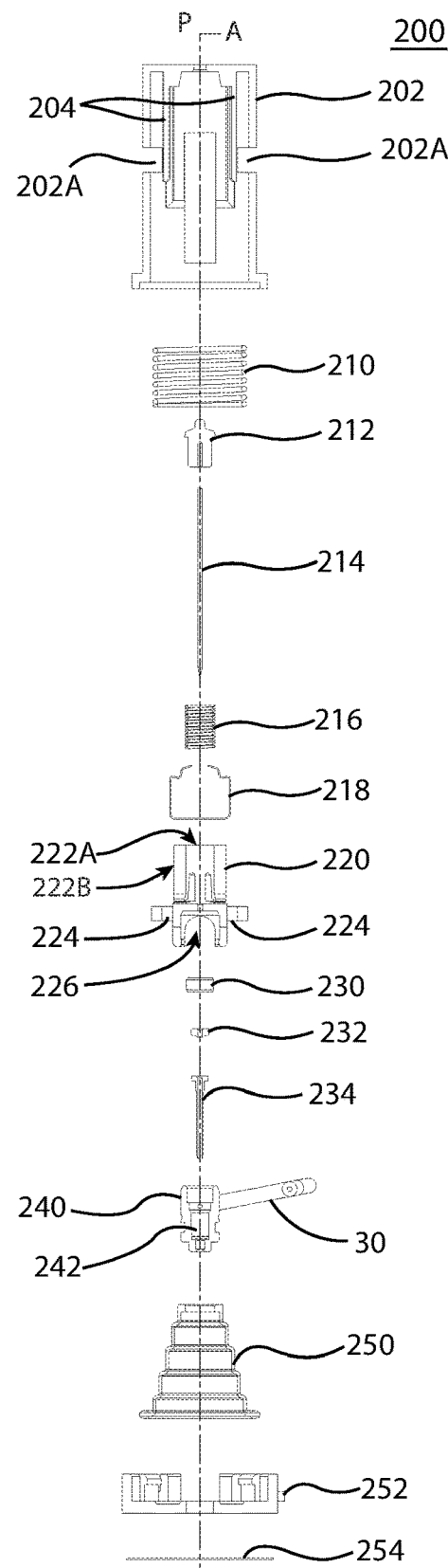
FIG. 3B shows a cross-sectional exploded view, exploded along an axis "A," of the insertion mechanism shown in FIG. 2A.

Insertion Mechanism:

The insertion mechanism 200 includes an insertion mechanism housing 202 having one or more lockout windows 202A, a base 252, and a sterile boot 250, as shown in FIG. 2A. Base 252 may be connected to assembly platform 20 to integrate the insertion mechanism into the drug pump 10 (as shown in FIG. 1B). The connection of the base 252 to the assembly platform 20 may be, for example, such that the bottom of the base is permitted to pass-through a hole in the assembly platform to permit direct contact of the base to the body of the user. In such configurations, the bottom of the base 252 may include a sealing membrane 254 that, at least in one embodiment, is removable prior to use of the drug pump 10. Alternatively, the sealing membrane 254 may remain attached to the bottom of the base 252 such that the needle 214 pierces the sealing membrane 254 during operation of the drug pump 10. As shown in FIGS. 3A and 3B, the insertion mechanism 200 may further include an insertion biasing member 210, a hub 212, a needle 214, a retraction biasing member 216, a clip 218, a manifold guide 220, a septum 230, a cannula 234, and a manifold 240. The manifold 240 may connect to sterile fluid conduit 30 to permit fluid flow through the manifold 240, cannula 234, and into the body of the user during drug delivery, as will be described in further detail herein.

The manifold guide 220 may include an upper chamber 222 and a lower chamber 226 separated by a manifold guide ring 228. The upper chamber 222 may include a clip interface slot 220A for engageable retention of clip 218. The upper chamber 222 may have an inner upper chamber 222A, within which the retraction biasing member 216, the clip 218, and the hub 212 may reside during an initial locked stage of operation, and an outer upper chamber 222B, which interfaces with the insertion biasing member 210. In at least one embodiment, the insertion biasing member 210 and the retraction biasing member 216 are springs, preferably compression springs. The hub 212 may be engageably connected to a proximal end of needle 214, such that displacement or axial translation of the hub 212 causes related motion of the needle 214.

As used herein, "needle" is intended to refer to a variety of needles including but not limited to conventional hollow needles, such as a rigid hollow steel needles, and solid core needles more commonly referred to as a "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. Upon assembly, the proximal end of needle 214 is maintained in fixed contact with hub 212, while the remainder of needle 214 is permitted to pass-through retraction biasing member 216, an aperture 218C of clip 218 (shown in FIG. 5A), and manifold guide 220. The needle 214 may further pass-through septum 230, cannula 234, manifold 240 through manifold header 242, sterile boot 250, and base 252 through base opening 252A. Septum 230, cannula 234, and manifold 240 may reside within lower chamber 226 of manifold guide 220 and within sterile boot 250 until operation of the insertion mechanism. In this position, the cannula 234 may reside over a distal portion of the needle 214 and held in place within the manifold header 242 of manifold 240 by a ferrule 232. Ferrule 232 ensures that cannula 234 remains substantially fixed and in sealed engagement within the manifold 240 to, for example, maintain the sterility of the manifold header 242. Similarly, septum 230 resides substantially fixed and in sealed engagement within the upper portion of the manifold 240 to maintain the sterility of the manifold header 242.

Figure 6A:
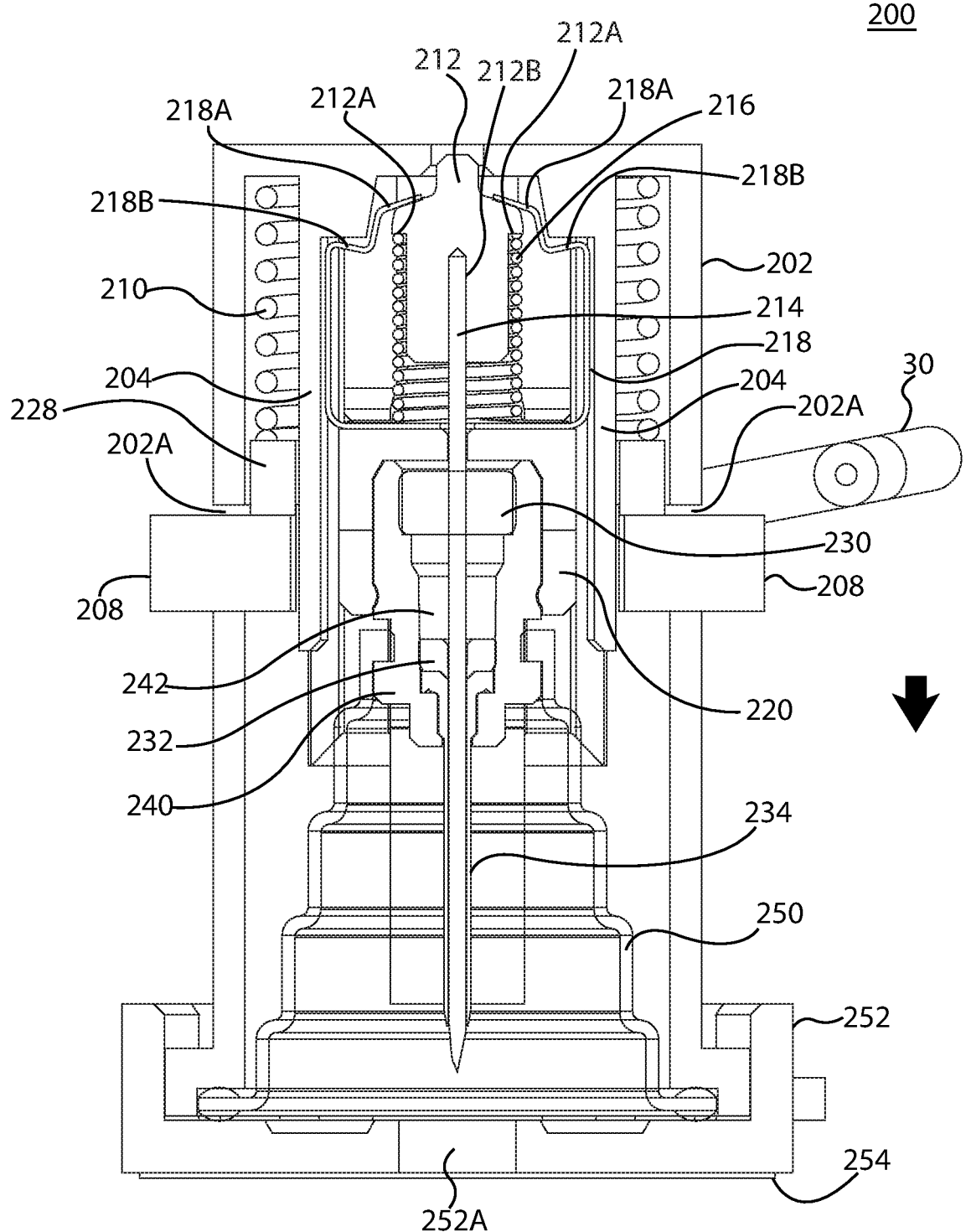
FIG. 6A shows a cross-sectional view of an insertion mechanism, according to a first embodiment of the present invention, in a locked and ready to use stage.
Figure 6B:
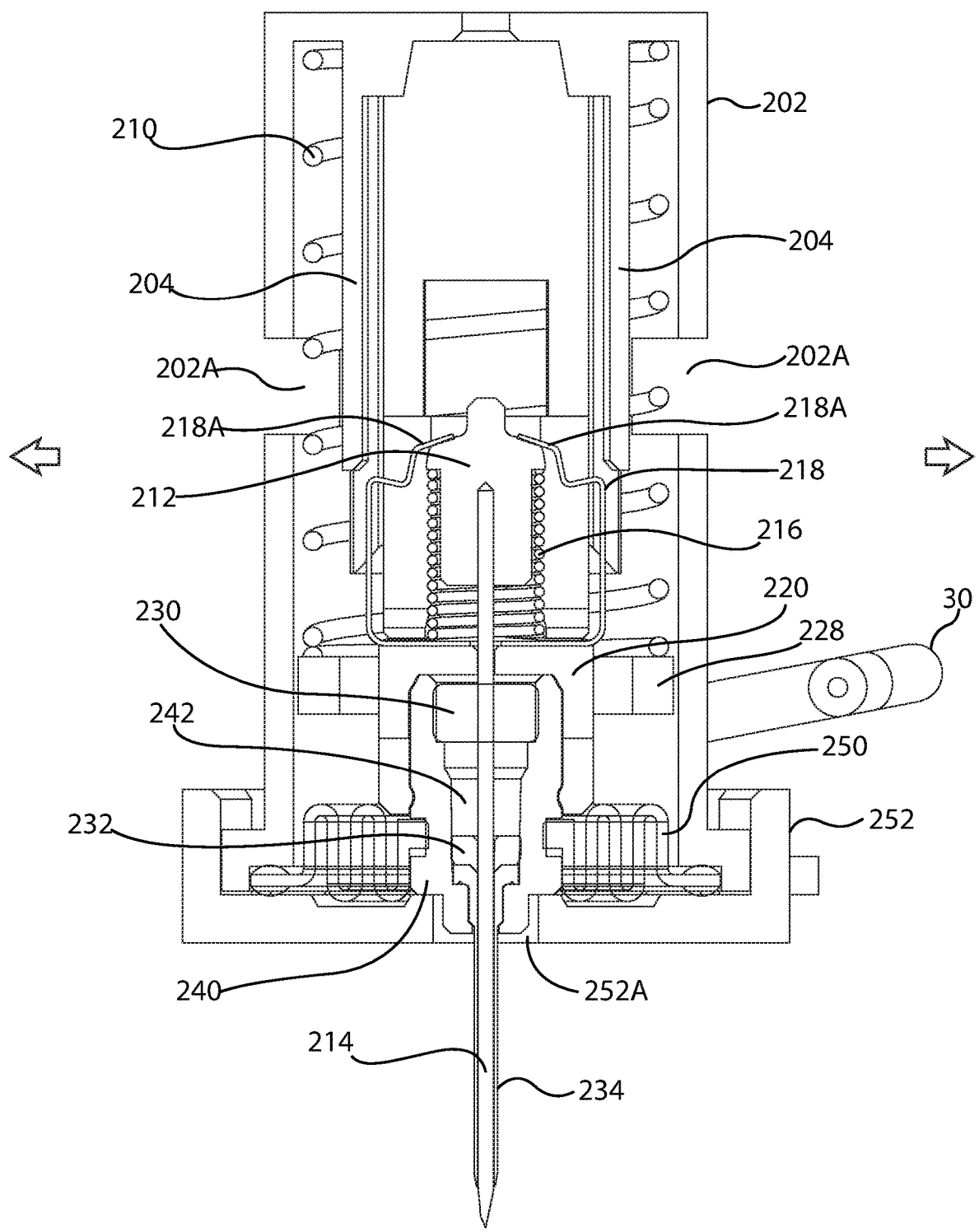
FIG. 6B shows a cross-sectional view of an insertion mechanism, according to a first embodiment of the present invention, in an unlocked and inserted stage.
Figure 6C:
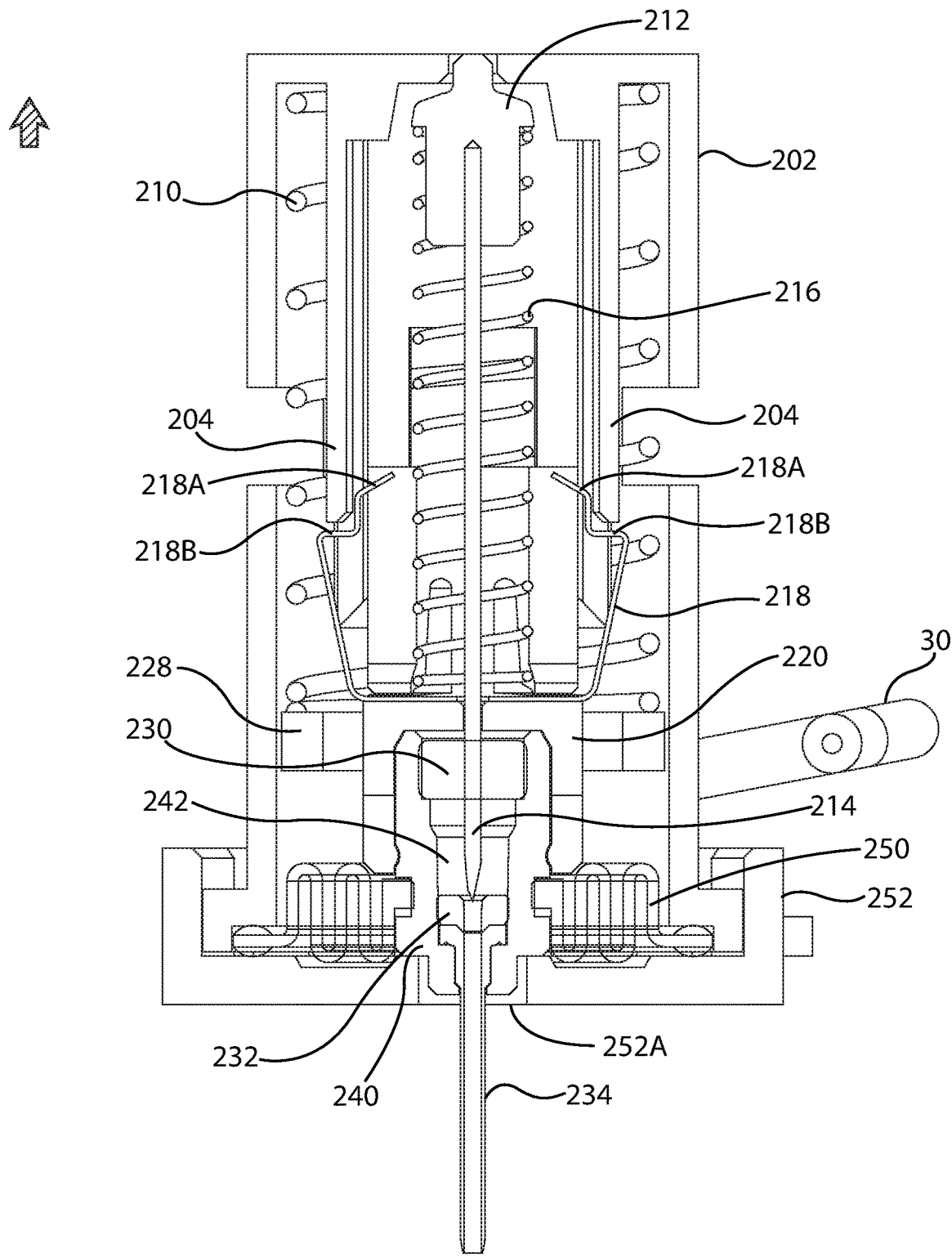
FIG. 6C shows a cross-sectional view of an insertion mechanism, according to a first embodiment of the present invention, in a retracted stage for drug delivery.

Sterile boot 250 is a collapsible or compressible sterile membrane that is in fixed engagement at a proximal end with the manifold 240 and at a distal end with the base 252. In at least on embodiment, the sterile boot 250 is maintained in fixed engagement at a distal end between base 252 and insertion mechanism housing 202, as shown in FIGS. 6A-6C. Base 252 includes a base opening 252A through which the needle and cannula may pass-through during operation of the insertion mechanism, as will be described further below. Sterility of the cannula and needle are maintained by their initial positioning within the sterile portions of the insertion mechanism. Specifically, as described above, needle 214 and cannula 234 are maintained in the sterile environment of the manifold header 242 and sterile boot 250. The base opening 252A of base 252 may be closed from non-sterile environments as well, such as by for example a sealing membrane 254.

Figure 4:
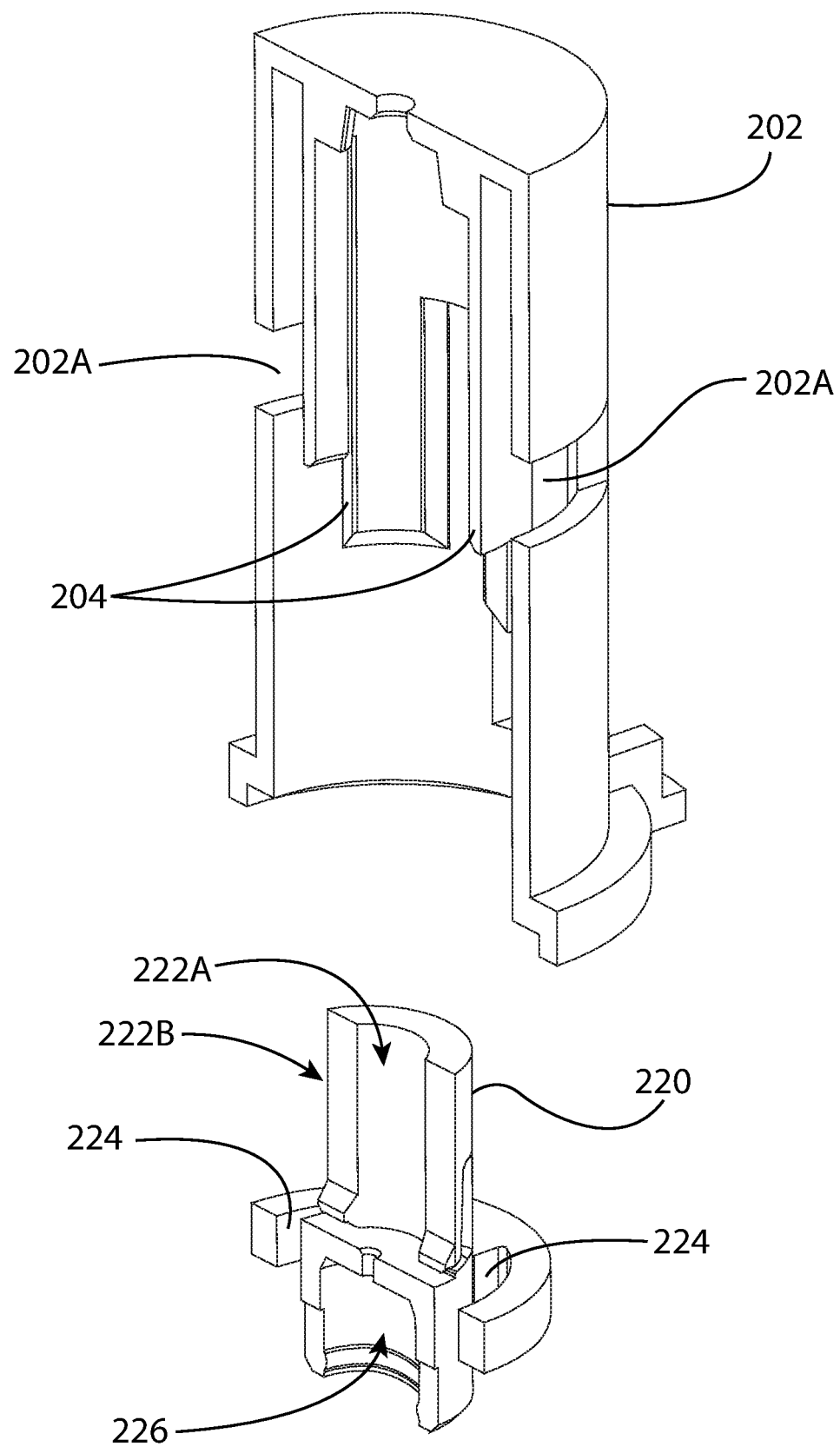
FIG. 4 shows a cross-section isometric view of the insertion mechanism housing and manifold guide of the insertion mechanism, according to a first embodiment of the present invention.

FIGS. 3A-3B, 4, and 5A-5C show the components of the insertion mechanism, according to at least a first embodiment, in greater detail. As shown in FIG. 4, insertion mechanism housing 202 may be a substantially cylindrical component having an inner chamber with guide protrusions 204. The guide protrusions 204 may be a pre-formed aspect on the interior of insertion mechanism housing 202, or may be a separate guide protrusion sleeve fixedly engaged to the interior proximal end of the insertion mechanism housing 202. The guide protrusions 204 slidably engage manifold guide 220 at pass-throughs 224 on manifold guide ring 228. The insertion biasing member 210 initially resides in an energized state between the guide protrusions 204 and inner surface of insertion mechanism housing 202 and between the interior proximal end of the insertion mechanism housing 202 and the manifold guide ring 228 of manifold guide 220. Therefore upon activation by the user, as described further hereinafter, the insertion biasing member 210 is caused to bear against and exert force upon manifold guide ring 228 of manifold guide 220 as the insertion biasing member 210 decompresses and/or de-energizes, causing axial translation in the distal direction of the manifold guide 220 and the components retained within its lower chamber 226. Prior to activation, the insertion biasing member 210 is maintained substantially above locking windows 202A in a compressed, energized state.

Figure 2B:
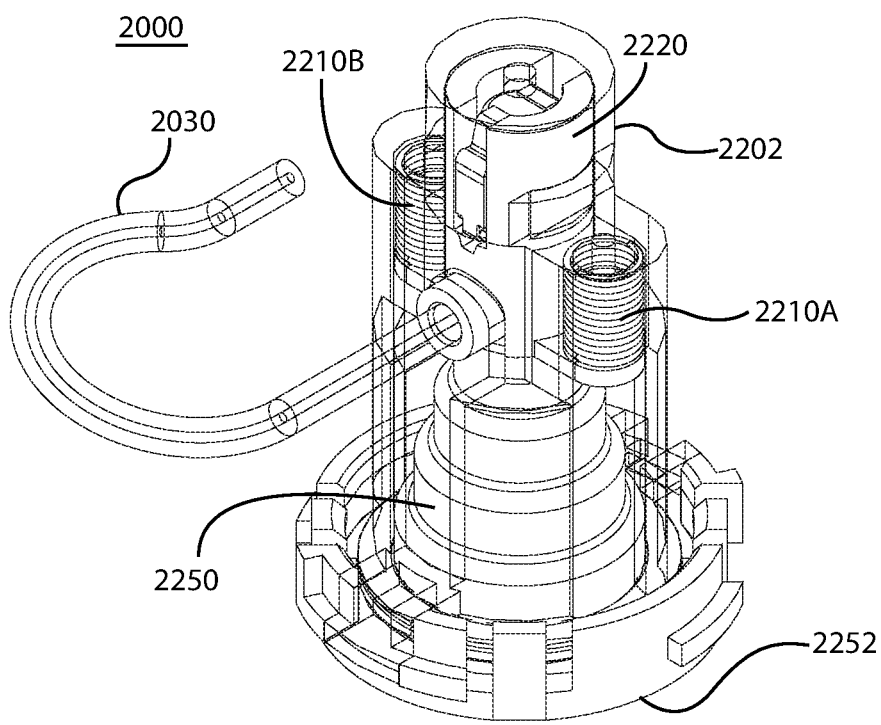
FIG. 2B shows an isometric view of an insertion mechanism, according to another embodiment of the present invention.

In an alternative embodiment of the insertion mechanism shown in FIG. 2B, the insertion mechanism 2000 may include two insertion biasing members 2210 A, B. Insertion mechanism 2000 further includes insertion mechanism housing 2202 (shown in transparent view), manifold guide 2220, sterile boot 2250, base 2252, and other components similar to those described above with reference to insertion mechanism 200. In the two insertion biasing members embodiment of the insertion mechanism shown in FIG. 2B, manifold guide ring includes two circular platforms upon which insertion biasing member 2210 A, B may bear. Insertion mechanism 2000 may function identically to insertion mechanism 200, but may provide additional insertion force through the use of multiple insertion biasing members 2210 A, B. The components and functions of the insertion mechanisms will be described further herein with the understanding that similar or identical components may be utilized for insertion mechanism 200, insertion mechanism 2000, and all reasonably understood variations thereof.

Figure 5A:
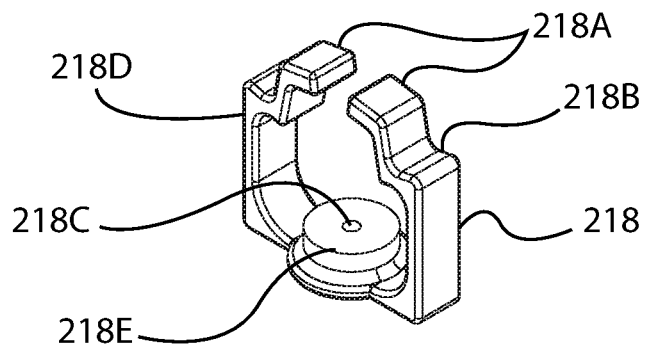
FIG. 5A shows an isometric view of a clip of the insertion mechanism, according to a first embodiment of the present invention.
Figure 5B:
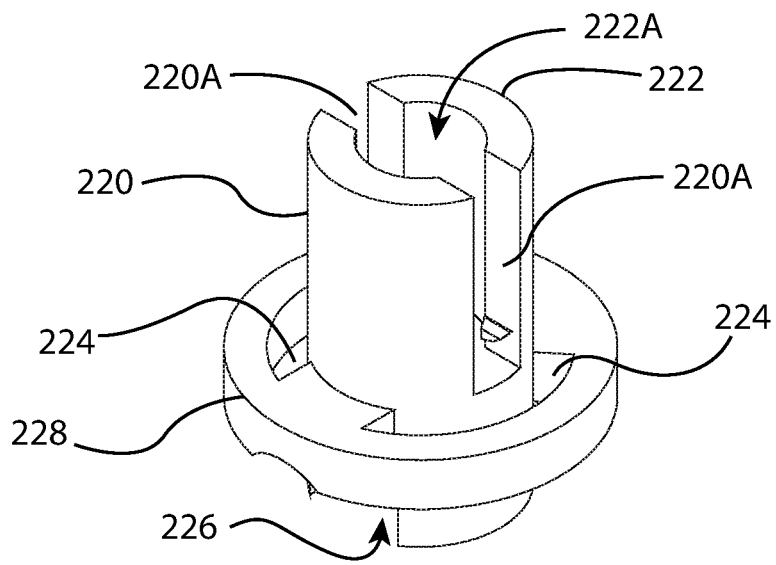
FIG. 5B shows an isometric view of the manifold guide shown in FIG. 4.
Figure 5C:
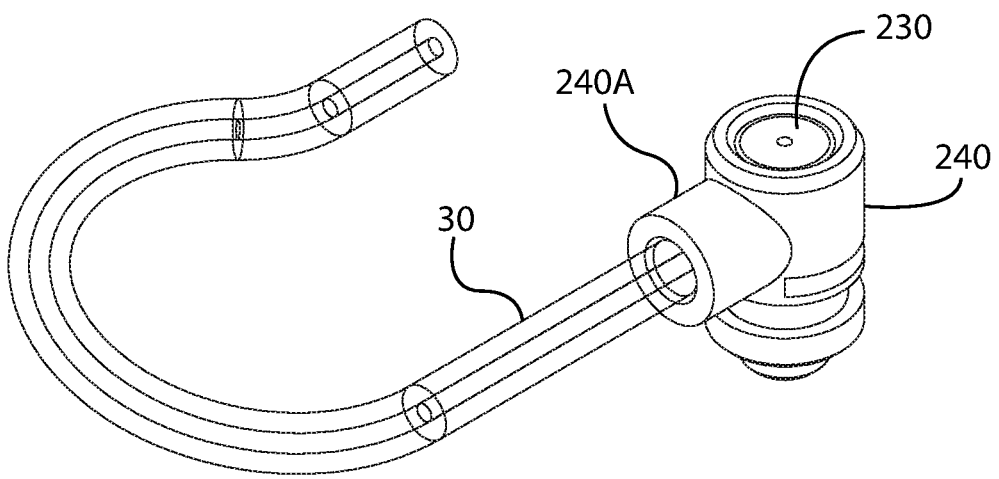
FIG. 5C shows an isometric view of a manifold, a manifold intake, and a fluid conduit of the insertion mechanism, according to a first embodiment of the present invention.

FIG. 5A shows a clip 218, according to one embodiment of the present invention. Clip 218 includes aperture 218C on platform 218E through which needle 214 may pass, and release surfaces 218A and lockout surfaces 218B of arms 218D. Clip 218 may be made of any number of resilient materials that are capable of flexing and returning to substantially their original form. In an original form, clip 218 may flex outwards such that arms 218D are not perpendicular with platform 218E. Clip 218 resides within clip interface slot 220A of manifold guide 220 such that clip 218 is in fixed engagement with manifold guide 220 but arms 218D are permitted to flex. In an initial locked stage, retraction biasing member 216 and hub 212 (with connected needle 214) are retained between release surfaces 218A and platform 218E of clip 218, and within inner upper chamber 222A of manifold guide 220 (shown in FIG. 4 and FIG. 5B). The needle may pass through aperture 218C of clip 218 and manifold guide 220 into septum 230 and manifold 240. Septum 230 resides within manifold 240, as shown in FIG. 5C. Manifold 240 further having a manifold wall which includes a manifold intake 240A through the manifold wall at which the sterile fluid conduit 30 may be connected. This connection is such that the sterility is maintained from the drug container 50 of the drive mechanism 100, through the fluid pathway connection 300 and the sterile fluid conduit 30, into sterile manifold header 242 of manifold 240 and sterile boot 250 to maintain the sterility of the needle 214, cannula 234, and the fluid pathway until insertion into the user for drug delivery.

The operation of the insertion mechanism is described herein with reference to the above components, in view of FIGS. 6A-6C. FIG. 6A shows a cross-sectional view of the insertion mechanism, according to at least one embodiment of the present invention, in a locked and ready to use stage. Lockout pin(s) 208 are initially positioned within lockout windows 202A of insertion mechanism housing 202. In this initial position, manifold guide ring 228 of manifold guide 220, clip 218, and hub 212 are retained above lockout windows 202A and locking pin(s) 208. In this initial configuration, insertion biasing member 210 and retraction biasing member 216 are each retained in their compressed, energized states.

As shown in FIG. 1B, the lockout pin(s) 208 (not visible) may be directly displaced by user depression of the activation mechanism 14. As the user disengages any safety mechanisms, such as an optional on-body sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows 202A of insertion mechanism housing 202. Displacement of the lockout pin(s) 208 permits insertion biasing member 210 to decompress and/or de-energize from its initial compressed, energized state.

As shown in FIG. 6A, hub ledges 212A maintain retraction biasing member 216 in a compressed, energized state between hub 212 and manifold guide 220 within inner upper chamber 222A. The hub 212 fixedly engages proximal end of needle 214 at hub recess 212B. Prior to operation, sealing member 254 may be removed from bottom of base 252 and base 252 is placed in contact with the target injection site on the body of the user. As lockout pin(s) 208 are displaced by the activation mechanism, as described above, and insertion biasing member 210 is permitted to expand axially in the distal direction (i.e., in the direction of the solid arrow in FIG. 6A), manifold ring guide 228 is forced by the decompression and/or de-energizing of the insertion biasing member 210 to translate axially in the distal direction to insert the needle 214 and cannula 234 into the body of the user. The axial translation of the manifold guide is directed, and maintained in rotational alignment, by interaction between the guide protrusions 204 of the insertion mechanism housing 202 and corresponding pass-throughs 224 of the manifold guide 220. Release surfaces 218A of clip 218 engage hub 212 and retain the retraction biasing member 216 in a compressed, energized state while the manifold guide 220 travels axially in the distal direction until the clip 218 reaches the end of the guide protrusions 204 where the clip 218 is permitted to flex outwards, as will be described further below.

FIG. 6B shows a cross-sectional view of an insertion mechanism in a needle inserted stage. As shown, sterile boot 250 is permitted to collapse as the insertion biasing member 210 expands and inserts the needle 214 and cannula 234 into the body of the user. At this stage, shown in FIG. 6B, needle 218 is introduced into the body of the user to place the cannula 234 into position for drug delivery. As shown in FIG. 6C, upon needle 214 and cannula 234 insertion by operation of the insertion biasing member 210 as described above, the needle 214 is retracted back (i.e., axially translated in the proximal direction) into the insertion mechanism housing 202. Manifold guide 220, clip 218, and guide protrusions 204 are dimensioned such that, as the manifold 240 substantially bottoms-out on base 252, i.e., reaches its full axial translation in the distal direction, the clip 218 escapes the guide protrusions 204 and is permitted to flex outwards (i.e., in the direction of the hollow arrows shown in FIG. 6B) to disengage release surfaces 218A from hub 212. Upon disengagement of the release surfaces 218A from hub 212, retraction biasing member 216 is permitted to expand axially in the proximal direction (i.e., in the direction of hatched arrow in FIG. 6C) from its initial compressed, energized state. The clip 218 is prevented from retracting or axial translation in the proximal direction by contact between the lockout surfaces 218B and the distal ends of the guide protrusions 204, as shown in FIG. 6C. This lockout also prevents axial translation in the proximal direction of the manifold guide 220 and insertion mechanism components that are distal to (i.e., below) the manifold guide ring 228.

Expansion of the retraction biasing member 216 translates hub 212, and needle 214 to which it is connected, axially in the proximal direction. Ferrule 232 retains cannula 234 inserted within the body of the user through base opening 252A. Upon retraction of the needle 214 from cannula 234, the fluid pathway from manifold header 242 to the body of the user through the cannula 234 is opened. As the fluid pathway connection is made to the drug container and the drive mechanism is activated, the fluid drug treatment is forced from the drug container through the fluid pathway connection and the sterile fluid conduit into the manifold header 242 and through the cannula 234 for delivery into the body of the user. Accordingly, activation of the insertion mechanism inserts the needle 214 and cannula 234 into the body of the user, and sequentially retracts the needle 214 while maintaining the cannula 234 in fluid communication with the body of the user. Retraction of the needle 214 also opens up the fluid pathway between the manifold header 242 and the body of the user through the cannula 234. At the end of the drug dose delivery, the cannula 234 may be removed from the body of the user by removal of the drug pump from contact with the user.

A method of operating an insertion mechanism according to the present invention includes: removing one or more lockout pins from corresponding one or more locking windows of an insertion mechanism housing, wherein removal of said lockout pins permits an insertion biasing member to expand from its initially energized state; driving, by expansion of the insertion biasing member, a manifold guide axially in the distal direction to force a needle and a cannula at least partially out of the insertion mechanism and into the body of a user; permitting outwards flexion of a clip retained in an upper chamber of the manifold guide, wherein said clip initially retains a hub and a retraction biasing member in an energized state and wherein flexion disengages one or more release surfaces of the clip from contact with a hub thereby permitting expansion of the retraction biasing member axially in the proximal direction; and retracting the needle upon retraction of the hub through a fixed connection between the needle and the hub, while maintaining the cannula inserted into the body of the user for fluid delivery.

Certain optional standard components or variations of insertion mechanism 200 or drug pump 10 are contemplated while remaining within the breadth and scope of the present invention. For example, upper or lower housings may optionally contain one or more transparent or translucent windows 18, as shown in FIGS. 1A-1C, to enable the user to view the operation of the drug pump 10 or verify that drug dose has completed. Additionally, the drug pump 10 may contain an adhesive patch 26 and a patch liner 28 on the bottom surface of the housing 12. The adhesive patch 26 may be utilized to adhere the drug pump 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug pump 10 in contact with the body of the user. Adhesive patch 26 may optionally include a protective shroud that prevents actuation of the optional on-body sensor 24 and covers base opening 252A. Removal of the patch liner 28 may remove the protective shroud or the protective shroud may be removed separately. Removal of the patch liner 28 may further remove the sealing membrane 254 of the insertion mechanism 200, opening the insertion mechanism to the body of the user for drug delivery.

Similarly, one or more of the components of insertion mechanism 200 and drug pump 10 may be modified while remaining functionally within the breadth and scope of the present invention. For example, as described above, while the housing of drug pump 10 is shown as two separate components upper housing 12A and lower housing 12B, these components may be a single unified component. Similarly, while guide protrusions 204 are shown as a unified pre-formed component of insertion mechanism housing 202, it may be a separate component fixedly attached to the interior surface of the insertion mechanism housing 202. As discussed above, a glue, adhesive, or other known materials or methods may be utilized to affix one or more components of the insertion mechanism and/or drug pump to each other. Alternatively, one or more components of the insertion mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the insertion mechanisms and drug pumps disclosed herein provide an efficient and easily-operated system for automated drug delivery from a drug container. The novel embodiments described herein provide integrated safety features; enable direct user activation of the insertion mechanism; and are configured to maintain the sterility of the fluid pathway. As described above, the integrated safety features include optional on-body sensors, redundant lockouts, automated needle insertion and retraction upon user activation, and numerous user feedback options, including visual and auditory feedback options. The novel insertion mechanisms of the present invention may be directly activated by the user. For example, in at least one embodiment the lockout pin(s) which maintain the insertion mechanism in its locked, energized state are directly displaced from the corresponding lockout windows of the insertion mechanism housing by user depression of the activation mechanism. Alternatively, one or more additional components may included, such as a spring mechanism, which displaces the lockout pin(s) upon direct displacement of the activation mechanism by the user without any intervening steps.

Furthermore, the novel configurations of the insertion mechanism and drug pumps of the present invention maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. A further benefit of the present invention is that the components described herein are designed to be modular such that, for example, housing and other components of the pump drug may readily be configured to accept and operate insertion mechanism 200, insertion mechanism 2000, or a number of other variations of the insertion mechanism described herein.

Assembly and/or manufacturing of insertion mechanism 200, drug pump 10, or any of the individual components may utilize a number of known materials and methodologies in the art. For example, a number of known cleaning fluids such as isopropyl alcohol may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

The insertion mechanism may be assembled in a number of methodologies. In one method, a hub is initially connected to a proximal end of a needle. The hub and needle are inserted into an inner upper chamber of a manifold guide, wherein a retraction biasing member is maintained in an energized state between the manifold guide and the hub. The hub, needle, and retraction biasing member are held in this alignment by a clip, wherein the clip is fixedly and flexibly connected to the manifold guide at a clip interface. A cannula is inserted into a manifold and held in place by a ferrule. A septum is inserted into the manifold at an end opposing the cannula to create a manifold header therebetween. The manifold, septum, cannula, and ferrule are inserted into a lower chamber of the manifold guide such that the needle pierces through the septum and resides within the cannula. The needle extends beyond the distal end of the cannula to provide a piercing tip. A sterile boot is connected to the manifold, wherein the needle and cannula reside within the sterile boot when the latter is in an expanded configuration.

An insertion spring is inserted into insertion mechanism housing between the housing and one or more guide protrusions extending into the interior of the housing from the proximal end. The manifold guide, having the components attached thereto as described herein, is inserted into the insertion mechanism housing such that the guide protrusions extend through corresponding pass-throughs on a manifold guide ring aspect of the manifold guide. As the manifold guide is translated in the proximal direction, the insertion biasing member is caused to contact the manifold guide ring and become energized. As translation of the manifold guide and compression of the insertion biasing member reach a point above one or more lockout windows of the insertion mechanism housing, one or more corresponding lockout pin(s) may be inserted to retain the manifold guide in this position and the insertion biasing member in the compressed, energized state.

The distal end of the sterile boot may be positioned and held in fixed engagement with the distal end of the insertion mechanism housing by engagement of the housing with a base. In this position, the sterile boot is in an expanded configuration around the needle and cannula and creates an annular volume which may be sterile. A fluid conduit may be connected to the manifold at a manifold intake such that the fluid pathway, when open travels directly from the fluid conduit, through the manifold intake, into the manifold header, and through the cannula upon retraction of the needle. A fluid pathway connection may be attached to the opposite end of the fluid conduit. The fluid pathway connection, and specifically a sterile sleeve of the fluid pathway connection, may be connected to a cap and pierceable seal of the drug container. The plunger seal and drive mechanism may be connected to the drug container at an end opposing the fluid pathway connection. A sealing membrane may be attached to the bottom of the base to close of the insertion mechanism from the environment. The components which constitute the pathway for fluid flow are now assembled. These components may be sterilized, by a number of known methods, and then mounted either fixedly or removable to an assembly platform or housing of the drug pump.

Manufacturing of a drug pump includes the step of attaching the base of the insertion mechanism to an assembly platform or housing of the drug pump. In at least one embodiment, the attachment is such that the base of the insertion mechanism is permitted to pass-through the assembly platform and/or housing to come in direct contact with the body of the user. The method of manufacturing further includes attachment of the fluid pathway connection, drug container, and drive mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the drug pump includes the steps of: activating, by a user, the activation mechanism; displacing a control arm to actuate an insertion mechanism; and actuating a power and control system to activate a drive control mechanism to drive fluid drug flow through the drug pump. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the drive control mechanism and drug container to force fluid drug flow through the drug container, the fluid pathway connection, a sterile fluid conduit, and the insertion mechanism for delivery of the fluid drug to the body of a user. The method of operation of the insertion mechanism and the drug pump may be better appreciated with reference to FIGS. 6A-6C, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. An insertion mechanism for a drug pump, said insertion mechanism comprising:
   an insertion mechanism housing having an internal chamber;
   a base connected to a distal end of the insertion mechanism housing;
   a manifold guide having a manifold guide ring, the manifold guide being disposed for axial translation within the insertion mechanism housing between an initial configuration and a needle insertion configuration;

one or more insertion biasing members held in an energized state within the internal chamber of the insertion mechanism housing between the insertion mechanism housing and the manifold guide ring when the manifold guide is in the initial configuration;

a needle having a proximal end;

a hub connected to the proximal end of the needle;

a retraction biasing member in an energized state between the hub and the manifold guide;

a manifold;

a septum;

a cannula;

an annular space within the manifold between the septum and the cannula defining a manifold header;

a sterile boot fixedly connected between the manifold and the base, an interior space being formed within the sterile boot between the manifold and the base, the cannula being disposed at least partially within the interior space, axial translation of the manifold guide within the insertion mechanism housing between the initial configuration and the needle insertion configuration translating the manifold, the septum, the cannula, the needle, the hub, and the retraction biasing member distally within the insertion mechanism housing.

2. The insertion mechanism of claim 1, wherein the sterile boot is compressible or collapsible, axial translation of the manifold guide within the insertion mechanism housing between the initial configuration and the needle insertion configuration at least partially compressing or collapsing the sterile boot as the manifold guide translates from the initial configuration and the needle insertion configuration.

3. The insertion mechanism of claim 1, wherein the sterile boot includes a proximal end and a distal end, the proximal end of the sterile boot being disposed in a fixed engagement with the manifold, and the distal end of the sterile boot being disposed in a fixed engagement with the base.

4. The insertion mechanism of claim 1, wherein the cannula is disposed at least partially about the needle.

5. The insertion mechanism of claim 4, wherein the base includes a base opening and a sealing membrane disposed within the base opening, axial translation of the manifold guide within the insertion mechanism housing between the initial configuration and the needle insertion configuration translating the cannula and the needle in a distal direction to pierce the sealing membrane.

6. The insertion mechanism of claim 1, further including a clip flexibly engaged with the manifold guide, the clip holding the retraction biasing member in the energized state between the hub and the manifold, axial translation of the manifold guide within the insertion mechanism housing between the initial configuration and the needle insertion configuration translating the clip holding the retraction biasing member in the energized state distally within the insertion mechanism housing.

7. The insertion mechanism of claim 1, wherein the manifold guide has an upper chamber and a lower chamber separated by the manifold guide ring, the manifold being disposed at least partially within the lower chamber of the manifold guide when the manifold guide is disposed in the insertion mechanism housing in both the initial configuration and the needle insertion configuration.

8. The insertion mechanism of claim 1, further comprising at least one lockout pin engaged with the manifold guide ring when the manifold guide is in the initial configuration to maintain the one or more insertion biasing members in the energized state, the at least one lockout pin being displaceable to disengage the manifold guide ring to allow the one or more insertion biasing members to at least partially de-energize and translate the manifold guide distally within the insertion mechanism housing to the needle insertion configuration.

9. The insertion mechanism of claim 8, wherein the insertion mechanism housing includes at least one lockout window, the at least one lockout pin extending through the at least one lockout window.

10. The insertion mechanism of claim 9, wherein the insertion mechanism housing includes a sidewall, the at least one lockout window being disposed in the sidewall.

11. The insertion mechanism of claim 8, wherein the manifold guide ring and the hub are disposed proximally to the at least one lockout pin.

12. A drug delivery pump with integrated safety features comprising a housing and an assembly platform, wherein an activation mechanism, a drive mechanism, a fluid pathway connection, a power and control system, and the insertion mechanism according to claim 1 are mounted to the assembly platform, the activation mechanism being disposed for selective activation to activate the insertion mechanism.

13. The drug delivery pump of claim 12, wherein depression of the activation mechanism causes displacement of at least one lockout pin engaged with the manifold guide ring to allow the one or more insertion biasing members to at least partially de-energize and translate the manifold guide distally within the insertion mechanism housing.

14. An insertion mechanism for a drug pump, said insertion mechanism comprising:

an insertion mechanism housing having an internal chamber;

a manifold guide having an upper chamber and a lower chamber separated by a manifold guide ring, the manifold guide being disposed for axial translation within the insertion mechanism housing between an initial configuration and a needle insertion configuration;

one or more insertion biasing members held in an energized state within the internal chamber of the insertion mechanism housing between the insertion mechanism housing and the manifold guide ring when the manifold guide is in the initial configuration;

a clip flexibly engaged with the upper chamber of the manifold guide;

a needle having a proximal end;

a hub connected to the proximal end of the needle;

a retraction biasing member, the clip holding the retraction biasing member in an energized state between the hub and the manifold guide;

a manifold at least partially disposed within the lower chamber of the manifold guide;

a septum;

a cannula disposed at least partially about the needle; and an annular space within the manifold between the septum and the cannula defining a manifold header;

axial translation of the manifold guide within the insertion mechanism housing between the initial configuration and the needle insertion configuration translating the manifold, the septum, the cannula, the needle, the hub, the clip, and the retraction biasing member distally within the insertion mechanism housing.

15. The insertion mechanism of claim 14, wherein the manifold is disposed at least partially within the lower chamber of the manifold guide when the manifold guide is disposed in the insertion mechanism housing in both the initial configuration and the needle insertion configuration.

16. The insertion mechanism of claim 14, further comprising at least one lockout pin engaged with the manifold guide ring when the manifold guide is in the initial configuration to maintain the one or more insertion biasing members in the energized state, the at least one lockout pin being displaceable to disengage the manifold guide ring to allow the one or more insertion biasing members to at least partially de-energize and translate the manifold guide distally within the insertion mechanism housing to the needle insertion configuration.

17. The insertion mechanism of claim 16, wherein the insertion mechanism housing includes at least one lockout window, the at least one lockout pin extending through the at least one lockout window.

18. The insertion mechanism of claim 17, wherein the insertion mechanism housing includes a sidewall, the at least one lockout window being disposed in the sidewall.

19. The insertion mechanism of claim 16, wherein the manifold guide ring and the hub are disposed proximally to the at least one lockout pin.

20. A drug delivery pump with integrated safety features comprising a housing and an assembly platform, wherein an activation mechanism, a drive mechanism, a fluid pathway connection, a power control system, and the insertion mechanism according to claim 14 are mounted to the assembly platform, the activation mechanism being disposed for selective activation to activate the insertion mechanism.

21. The drug delivery pump of claim 20, wherein depression of the activation mechanism causes displacement of at least one lockout pin engaged with the manifold guide ring to allow the one or more insertion biasing members to at least partially de-energize and translate the manifold guide distally within the insertion mechanism housing.

* * * * *